United States Patent [19]
Lantero et al.

[11] Patent Number: 5,541,097
[45] Date of Patent: *Jul. 30, 1996

[54] METHOD FOR PREPARING IMMOBILIZED ENZYME CONJUGATES AND IMMOBILIZED ENZYME CONJUGATES PREPARED THEREBY

[75] Inventors: Oreste J. Lantero, Goshen; Jack W. Brewer, Elkhart; Sharon M. Sarber, Bristol, all of Ind.

[73] Assignee: Solvay Enzymes, Inc., Elkhart, Ind.

[ * ] Notice: The term of this patent shall not extend beyond the expiration date of Pat. No. 5,472,861.

[21] Appl. No.: 385,831

[22] Filed: Feb. 9, 1995

Related U.S. Application Data

[63] Continuation of Ser. No. 370,220, Jan. 9, 1995, Pat. No. 5,472,861, which is a continuation of Ser. No. 114,143, Sep. 1, 1993, abandoned.

[51] Int. Cl.$^6$ .............................. C12N 9/96; C12N 9/26; C12N 11/00; C12N 11/14
[52] U.S. Cl. .......................... 435/188; 435/179; 435/175; 435/176; 435/177; 435/180; 435/181; 435/201; 435/202; 435/204; 435/205; 530/810
[58] Field of Search ..................................... 435/174, 175, 435/176, 177, 178, 179, 180, 181, 201, 202, 203, 204, 205, 210, 188; 530/810, 811, 812, 815, 816

[56] References Cited

U.S. PATENT DOCUMENTS

| | | | |
|---|---|---|---|
| 4,355,105 | 10/1982 | Lantero, Jr. .............................. | 435/94 |
| 4,411,999 | 10/1983 | Shigesada et al. ...................... | 435/177 |
| 4,713,333 | 12/1987 | Chiang et al. ............................ | 435/96 |

FOREIGN PATENT DOCUMENTS

| | | |
|---|---|---|
| 0216272 | 4/1987 | European Pat. Off. . |
| 0215272 | 4/1987 | European Pat. Off. . |
| 5743687 | 5/1978 | Japan . |

OTHER PUBLICATIONS

Broun "Chemically Aggregated Enzymes" from Meth. Enzymol. vol. XLIV 263–280.

Wingard, Lemuel, "Enzyme Engineering", *Biotechnology and Bioengineering Symposium*, No. 3, (1972).

Food Chemicals Codex, Third Edition (1981), pp. 484–485.

Zemek, J., "Crosslinked Polyethylenimine: An Enzyme Carrier with Spacers of Various Lengths Introduced in Crosslinking Reaction", *Enzyme Microb. Technol.*, 1982, vol. 4, Jul., pp. 233–235.

Emneus, J., et al., "Comparison Between Different Inorganic Supports for the Immobilization of Amyloglucosidase and α–lamylase To be Used in Enzyme Reactors in Flow–Injection Systems", *Analy. Chim. Acta*, 276:303–318, 1993.

*Primary Examiner*—Mindy Fleisher
*Assistant Examiner*—Nancy J. Degen
*Attorney, Agent, or Firm*—McDermott, Will & Emery

[57] ABSTRACT

A method for preparing an immobilized enzyme conjugate, whereby the enzyme is treated with a polyfunctional amine reactive material for forming a treated enzyme-containing adduct before being immobilized on a solid support which has been contacted with a solution of a polyamine compound. The method is especially preferred for use with glucoamylase, fungal α-amylase and β-amylase. Immobilized enzyme conjugates formed by use of this method include treated enzyme-containing adducts. The immobilized enzyme conjugates disclosed herein are more stable and the enzymes immobilized therein are more tightly-held than those otherwise obtained and provided.

22 Claims, No Drawings

5,541,097

METHOD FOR PREPARING IMMOBILIZED ENZYME CONJUGATES AND IMMOBILIZED ENZYME CONJUGATES PREPARED THEREBY

This is a continuation of application Ser. No. 08/370,220 filed Jan. 9, 1995, now U.S. Pat. No. 5,472,861, which in turn is a continuation application of Ser. No. 08/114,143 filed Sep. 1, 1993 now abandoned.

FIELD OF THE INVENTION

The present invention relates to a method for preparing immobilized enzyme conjugates and to stable, immobilized enzyme conjugates which are prepared by use of this method.

BACKGROUND OF THE INVENTION

Generally, enzymes are water soluble. Thus, when utilized in a reaction medium without being immobilized on a support (free enzyme), they are difficult to remove therefrom for reuse. These difficulties result in increased costs associated with the use of such enzymes due to the necessity for their frequent replacement. Moreover, while free (unimmobilized) enzymes can be used efficiently in batch-type processes, they do not lend themselves to use in continuous, industrial-scale processes.

To reduce the high cost of enzyme replacement, various methods have been devised for immobilizing enzymes prior to their use. Such immobilization permits the enzymes to be conviently removed from the reaction medium for subsequent reuse. These immobilized enzymes may be employed in various reactor systems, such as in packed columns and stirred tank reactors, depending on the nature of the substrate which is being biocatalytically reacted.

Methods proposed for immobilization of an enzyme include the use of a carrier in the form of a solid support made from inorganic or organic material. Such materials include, for example, gamma-alumina, titania, activated granular carbon, granular diatomaceous earth, glass beads, porous glass, pumice-stone, silica gel, metal oxide and aluminium oxide. A compound, or a mixture of compounds, is used to attach the enzyme to this carrier, with polyethylenimine and glutaraldehyde in particular being cited. However, such methods can be disadvantageous in that the enzyme is not tightly-held (by either being bonded thereto or being entrapped therein) to the carrier. Thus, the enzyme can become "detached" (unbonded) from the carrier becoming "free" in the reaction medium. In fact, the forces which exist between the enzyme and the carrier so as to hold them together are often quite weak, such that the enzyme is readily desorbed from the carrier in the presence of the substrate being processed, and lost in the reaction medium.

U.S. Pat. No. 4,713,333 discloses a process wherein enzymes are immobilized on granular diatomaceous earth. That process involves contacting porous granular diatomaceous earth with a solution of polyethylenimine. Then, the diatomaceous earth containing the polyethylenimine is contacted with glutaraldehyde. Finally, an aqueous solution of the enzyme is then added thereto, whereby the enzyme is immobilized thereon. While being particularly useful, immobilized enzymes conjugates formed in this manner can nonetheless still be improved in view of their stability and half-life.

Thus, it can be seen that there remains a need for a method for immobilizing enzymes in an enzyme conjugate, so that the enzyme is tightly-held (or maintained) within the conjugate formed thereby, whereby the immobilized enzyme cannot become "detached" from the remainder of the conjugate and lost in the reaction medium. It can further be seen that there remains a need for immobilized enzyme conjugates in which the enzyme is tightly-held thereto and/or therein (stable), so that during the use of such conjugates, the enzyme loss therefrom to the reaction medium is reduced, whereby a significant improvement in the productivity thereof is realized.

SUMMARY OF THE INVENTION

It is a primary object of the present invention to provide a method for preparing immobilized enzyme conjugates, wherein the enzyme is tightly-held (stable) within and/or to the immobilized enzyme conjugates prepared thereby.

It is a further primary object of the present invention to provide a method for preparing immobilized enzyme conjugates, so that the immobilized enzyme conjugates obtained thereby are not inactivated, and further so that the immobilized enzyme conjugates prepared thereby exhibit an improved half-life over those obtained by the use of other methods.

It is a still further primary object of the present invention to provide immobilized enzyme conjugates which exhibit an improved half-life over those obtained by the use of other methods, so that a significant improvement in the productivity thereof is realized.

It is a further primary object of the present invention to provide immobilized enzyme conjugates which are stable, in that the enzyme of the conjugate is tightly-held within (or to) the conjugate, so that enzyme loss to the reaction medium is reduced.

In accordance with the teachings of the present invention, a method of preparing an immobilized enzyme conjugate is disclosed. This method includes contacting a solid support, such as porous granular diatomaceous earth, with a solution of a polyamine compound having at least one pendant amine group. In this manner, a carrier is obtained. An enzyme is contacted with a solution of at least one amine reactive material, whereby the enzyme is treated. This amine reactive material is selected from the group consisting of polyfunctional aldehydes, polyfunctional organic halides, polyfunctional anhydrides, polyfunctional azo compounds, polyfunctional isothiocyanates, polyfunctional isocyanates and blends of two or more of these amine reactive materials. In this manner, a treated enzyme-containing adduct (sometimes hereinafter also referred to as the "treated adduct") is formed. Finally, the carrier and the treated adduct are bought into contact with one another, so that the carrier and the treated adduct form a stable, active immobilized enzyme conjugate (sometimes herein after variously referred to as "immobilized conjugate", "enzyme conjugate" "treated enzyme-containing conjugate", "treated conjugate" and "conjugate"). In this respect, it is preferred that the carrier and the treated adduct react, so that the amine reactive material of the treated adduct is bonded to the polyamine compound of the carrier.

It is preferred that the carrier is washed before being bought into contact with the treated adduct, so that excess amounts of the polyamine compound is removed therefrom.

Preferably, the polyamine compound is chosen from the group consisting of polyethylenediamine; a polyethylenimine (such as, for example, polydiethylenetriamine, polytriethylenetetramine, polypentaethylenehexamine or polyhexamethylenediamine); polymethylenedicyclohexylamine; polymethylenedianiline; polytetraethylenepentamine; polyphenylenediamine and blends of two or more of these polyamine compounds. It is further preferred that the polyamine compound be chosen from those compounds enumerated above which have a molecular weight of 500–100,000 daltons and are water soluble. It is most preferred that the polyamine compound be polyethylenimine.

Preferably, the amine reactive material is selected from the group consisting of polyfunctional aldehydes, polyfunctional organic halides, polyfunctional anhydrides, polyfunctional azo compounds, polyfunctional isothiocyanates, polyfunctional isocyanates and blends of two or more of these amine reactive materials. It is further preferred that the amine reactive material is selected from the group consisting of glutaraldehyde, succindialdehyde, terephthaldehyde, bisdiazobenzidine-2,2'-disulfonic acid, 4,4'-difluoro-3,3'-dinitrodiphenylsulfone, diphenyl-4,4'-dithiocyanate- 2,2'-disulfonic acid, 3-methoxydiphenylmethane-4,4'-diisocyanate, toluene-2-isocyanate-4-isothiocyanate, toluene-2,-4-diisothiocyanate, diazobenzidine, diazobenzidine-3,3'-dianisidine, N,N'-hexamethylene bisiodoacetamide, hexamethylene diisocyanate, cyanuric chloride, 1,5-difluoro-2,4-dinitrobenzene and blends or two or more of these amine reactive materials. Still further preferred is that the amine reactive material be selected from the group consisting of polyfunctional aldehydes. More preferably, the amine reactive material is selected from the group consisting of glutaraldehyde, succindialdehyde, terephthaldehyde. Best results have been obtained with glutaraldehyde.

It is yet further preferred that the ratio between the treated enzyme-containing adduct and the washed carrier to be from about 0.05 ml to about 0.6 ml of treated adduct per gram of the carrier. It is yet further preferred that the ratio between the amine reactive material and the enzyme is from about 0.10 g to about 1.50 g of the amine reactive material per ml of the enzyme.

In a preferred embodiment, the enzyme is contacted with the solution of an amine reactive material under conditions which include agitation.

In another preferred embodiment, the immobilized enzyme conjugate is washed with water after being formed.

The method disclosed herein is useful for preparing immobilized enzyme conjugates of any enzyme containing an amino group capable of reacting with the amine reactive material. Also two or more enzymes can be immobilized. These enzymes include trypsin, papain, hexokinase, ficin, bromelin, lactic acid dehydrogenase, lactase, glucose isomerase, glucoamylase, chymotrypsin, pronase, acylase, invertase, amylase, pullulanase, transglucosidase, glucose oxidase, pepsin, protease, catalase, hydrolase, rennin, transferase and mixtures thereof. These enzymes include preferably glucose isomerase, glucoamylase, invertase, β-amylase, bacterial α-amylase, fungal α-amylase, transglucosidase and mixtures thereof. These enzymes include more preferably glucoamylase, bacterial α-amylase, fungal α-amylase, β-amylase and mixtures thereof. Good results have been obtained with the glucoamylase sold under the trademark DIAZYME L-200 by SOLVAY ENZYMES, Inc. (Elkhart, Ind.). Good results have also been obtained with the fungal α-amylase sold under the trademark CLARASE L-40,000 by SOLVAY ENZYMES, Inc. (Elkhart, Ind.). Finally, good results have further been obtained with the β-amylase sold under the trademark SPEZYME BBA 1500.

In accordance with the teachings of the present invention, a method is disclosed for preparing an immobilized glucoamylase conjugate. This method includes contacting solid support with a solution of a polyethylenimine. In this manner, a carrier is obtained. The glucoamylase is contacted with a solution of glutaraldehyde, whereby the glucoamylase is treated. In this manner, a treated glucoamylase-containing adduct is formed. Finally, the carrier and the treated glucoamylase-containing adduct are bought into contact with one another, such that the carrier and the treated glucoamylase-containing adduct react forming a stable, active immobilized glucoamylase conjugate.

Preferably, the solid support is porous. Most preferably, the solid support is porous granular diatomaceous earth.

In further accordance with the teachings of the present invention, a method is disclosed for preparing an immobilized fungal α-amylase conjugate. This method includes contacting a solid support with a solution of a polyethylenimine. In this manner, a carrier is obtained. The fungal α-amylase is contacted with a solution of glutaraldehyde, whereby the α-amylase is treated. In this manner, a treated α-amylase-containing adduct is formed. Finally, the carrier and the treated α-amylase-containing adduct are bought into contact with one another, such that the carrier and the treated α-amylase-containing adduct react forming a stable, active immobilized fungal α-amylase conjugate.

In still further accordance with the teachings of the present invention, a method is disclosed for preparing an immobilized β-amylase conjugate. This method includes contacting a solid support with a solution of a polyethylenimine. In this manner, a carrier is obtained. The β-amylase is contacted with a solution of glutaraldehyde, whereby the β-amylase is treated. In this manner, a treated β-amylase-containing adduct is formed. Finally, the carrier and the treated β-amylase-containing adduct are bought into contact with one another, such that the carrier and the treated β-amylase adduct react forming a stable, active immobilized β-amylase conjugate.

In another aspect of the present invention, disclosed herein are stable, active immobilized enzyme conjugates which exhibit an improved half-life over those obtained by other methods, so that a significant improvement in the productivity thereof is realized.

In accordance with the teachings of the present invention, immobilized enzyme conjugates are disclosed. These immobilized enzyme conjugates include a carrier and a treated adduct. The carrier includes a polyamine compound having at least one pendant amine group. A solid support is bonded to the polyamine compound, whereby the carrier is formed. The treated adduct includes at least one amine reactive material. This amine reactive material is selected from the group consisting of polyfunctional aldehydes, polyfunctional organic halides, polyfunctional anhydrides, polyfunctional azo compounds, polyfunctional isothiocyanates, polyfunctional isocyanates and blends of two or more of these amine reactive materials. At least one enzyme is bonded to the (at least one) amine reactive material, whereby the enzyme is treated and the treated enzyme-containing adduct is formed. Finally, the carrier is bonded to the treated adduct including the treated enzyme, whereby a stable, active immobilized enzyme conjugate is formed.

Preferably, the solid support is porous. It is especially preferred that the solid support be porous granular diatomaceous earth.

Preferably, the polyamine compound is chosen from the group consisting of polyethylenediamine; a polyethylenimine (such as, for example, polydiethylenetriamine, polytriethylenetetramine, polypentaethylenehexamine or polyhexamethylenediamine); polymethylenedicyclohexylamine; polymethylenedianiline; polytetraethylenepentamine; polyphenylenediamine and blends of two or more of these polyamine compounds. It is further preferred that the polyamine compound be chosen from those compounds enumerated above which have a molecular weight of 500–100,000 daltons and are water soluble. It is most preferred that the polyamine compound be polyethylenimine.

Preferably, the amine reactive material is selected from the group consisting of polyfunctional aldehydes, polyfunctional organic halides, polyfunctional anhydrides, polyfunctional azo compounds, polyfunctional isothiocyanates, polyfunctional isocyanates and blends of two or more of these amine reactive materials. It is further preferred that the amine reactive material is selected from the group consisting of glutaraldehyde, succindialdehyde, terephthaldehyde, bisdiazobenzidine-2,2'-disulfonic acid, 4,4'-difluoro-3,3'-dinitrodiphenylsulfone, diphenyl-4,4'-dithiocyanate-2,2'-disulfonic acid, 3-methoxydiphenylmethane-4,4'-diisocyanate, toluene-2-isocyanate-4-isothiocyanate, toluene-2,-4-diisothiocyanate, diazobenzidine, diazobenzidine-3,3'-dianisidine, N,N'-hexamethylene bisiodoacetamide, hexamethylene diisocyanate, cyanuric chloride, 1,5-difluoro-2,4-dinitrobenzene and blends or two or more of these amine reactive materials. Still further preferred is that the amine reactive material be selected from the group consisting of polyfunctional aldehydes. More preferably, the amine reactive material is selected from the group consisting of glutaraldehyde, succindialdehyde, terephthaldehyde. Best results have been obtained with glutaraldehyde.

It is still further preferred that the ratio between the treated enzyme-containing adduct and the carrier to be from about 0.05 ml to about 0.6 ml of treated adduct per gram of the carrier. It is still yet further preferred that the ratio between the amine reactive material and the enzyme is from about 0.10 g to about 1.50 g of the amine reactive material per ml of the enzyme.

The immobilized enzyme conjugate disclosed herein may include any enzyme containing an amino group that is capable of reacting with the amine reactive material.

In accordance with the teachings of the present invention, an immobilized glucoamylase conjugate is disclosed. This immobilized glucoamylase conjugate includes a carrier and a treated adduct. The carrier includes polyethylenimine. A solid support is bonded to the polyethylenimine, whereby the carrier is formed. The treated adduct includes glutaraldehyde. Glucoamylase is bonded to the glutaraldehyde, whereby the glucoamylase is treated and the treated adduct is formed. Finally, the carrier is bonded to the treated adduct including the treated glucoamylase, whereby a stable, active immobilized glucoamylase conjugate is formed.

In further accordance with the teachings of the present invention, an immobilized fungal α-amylase conjugate is disclosed. This immobilized fungal α-amylase includes a carrier and a treated adduct. The carrier includes polyethylenimine. A solid support is bonded to the polyethylenimine, whereby the carrier is formed. The treated adduct includes glutaraldehyde. Fungal α-amylase is bonded to the glutaraldehyde, whereby the fungal α-amylase is treated and the treated adduct is formed. Finally, the carrier is bonded to the treated α-amylase-containing adduct, whereby a stable, active immobilized fungal α-amylase conjugate is formed.

In still further accordance with the teachings of the present invention, an immobilized β-amylase conjugate is disclosed. This immobilized β-amylase conjugate includes a carrier and a treated adduct. The carrier includes polyethylenimine. A solid support is bonded to the polyethylenimine, whereby the carrier is formed. The treated adduct includes glutaraldehyde. β-amylase is bonded to the glutaraldehyde, whereby the β-amylase is treated and the treated adduct is formed. Finally, the carrier is bonded to the treated β-amylase-containing adduct, whereby a stable, active immobilized β-amylase conjugate is formed.

In accordance with the teachings of the present invention, an immobilized enzyme conjugate comprising a carrier and a treated adduct is disclosed. The treated adduct includes at least one amine reactive material selected from the group consisting of polyfunctional aldehydes, polyfunctional organic halides, polyfunctional anhydrides, polyfunctional azo compounds, polyfunctional isothiocyanates, polyfunctional isocyanates and blends of two or more of these amine reactive materials. The treated adduct further includes at least one enzyme bonded to the at least one amine reactive material. In this manner, the enzyme is treated and a treated enzyme-containing adduct is formed. Finally, the carrier is bonded to the treated enzyme-containing adduct, whereby a stable, active immobilized enzyme conjugate is formed.

In still another aspect of the present invention, a treated adduct for use in preparing an immobilized enzyme conjugate is disclosed. The treated adduct includes at least one amine reactive material selected from the group consisting of polyfunctional aldehydes, polyfunctional organic halides, polyfunctional anhydrides, polyfunctional azo compounds, polyfunctional isothiocyanates, polyfunctional isocyanates and blends of two or more of these amine reactive materials. The treated adduct further includes at least one enzyme bonded to the at least one amine reactive material. In this manner, the enzyme is treated and a treated enzyme-containing adduct is formed.

These and other objects and advantages of the present invention will become readily apparent from a reading of the following description of the present invention in conjunction with the illustrative examples.

DESCRIPTION OF PREFERRED EMBODIMENTS

The method of the present invention is useful for the preparation of novel immobilized enzyme conjugates which are active and stable, with the enzymes thereof tightly held therein.

Enzymes for which the method disclosed herein is useful include any enzyme containing an amino group capable of reacting with the amine reactive material. Also two or more enzymes can be immobilized in the same conjugate. These enzymes include trypsin, papain, hexokinase, ficin, bromelin, lactic acid dehydrogenase, lactase, glucose isomerase, glucoamylase, chymotrypsin, pronase, acylase, invertase, amylase, pullulanase, transglucosidase, glucose oxydase, pepsin, protease, catalase, hydrolase, rennin, transferase and mixtures thereof. These enzymes include preferably glucose isomerase, glucoamylase, invertase, β-amylase, bacterial α-amylase, fungal α-amylase, transglucosidase and mixtures thereof. These enzymes include more preferably glucoamylase, bacterial α-amylase, fungal α-amylase, β-amylase and mixtures thereof. Good results have been obtained with the glucoamylase sold under the trademark DIAZYME L-200 by SOLVAY ENZYMES, Inc. (Elkhart, Ind.). Good results have also been obtained with the fungal α-amylase sold under the trademark CLARASE L-40,000 by SOLVAY ENZYMES, Inc. (Elkhart, Ind.). Further good results have been obtained with the β-amylase sold under the trademark SPEZYME BBA 1500.

The method of the present invention differs from those previously disclosed in that it includes a step of contacting the enzyme with a solution of an amine reactive material, such as glutaraldehyde, to form a (a treated enzyme-containing) treated adduct, before the treated enzyme-containing adduct is bonded to the carrier. While not precisely understood, it is believed that, in this manner, the enzyme is treated before being reacted (bonded) with the carrier, so that when the treated adduct is subsequently contacted (reacted) with the carrier, the treated enzyme is more tightly-bonded and/or more tightly-held (entrapped) in the immobilized enzyme conjugate formed thereby [as measured by the amount (quantity) of enzymatic activity that is present in the reaction medium after the immobilized conjugate is removed therefrom. Such amount Of enzymatic activity is equal to that enzymatic activity which was lost from the enzyme conjugate to the reaction medium during the use of the conjugate].

As used herein with reference to the contacting of the enzyme with the amine reactive material to form the adduct and the compounds, compositions and components formed thereby, the term "treated" refers to the actual process of contacting the enzyme and the amine reactive material to form the adduct, as well as to the structure of the enzyme, compound and/or composition which is formed as a result of such contact (or treatment). Thus, for example, as used herein, a "treated" enzyme will have been an enzyme that has been contacted with the amine reactive material, as described herein, and, as a result of such contact, will have been formed into a compound having more "holding" forces, such as (for illustration only) strong (tight) covalent bonds involving, and/or cross-linkages involving and/or entrapping the enzyme.

By utilizing the method of the invention, it is possible to provide immobilized enzyme conjugates which exhibit improved long term stability as well as increased total activity.

The immobilized enzyme conjugates of the present invention include a carrier and a treated enzyme-containing adduct. In these conjugates, the enzyme is treated by contact (reaction) with the amine reactive material(s) of the adduct before the treated enzyme-containing adduct is bonded to a carrier. It is believed that such treatment of the enzyme results in the immobilized enzyme conjugate having: (1) an increased number of bonds, including covalent bonds, involving the conjugate and/or the enzyme thereof; and/or (2) an increased cross-linking between the treated enzyme and the remainder of the immobilized enzyme conjugate, thereby providing a matrix (or an improved matrix) which tightly-holds (or traps) the enzyme therein.

The preferred method disclosed herein involves the formation of the carrier separately from the treated adduct by contacting a solid support with a solution of a polyamine compound having at least one pendant amine group. Such a step, wherein the solid support is porous granular diatomaceous earth is well described in the U.S. Pat. No. 4,713,333, the contents of which are hereby incorporated by reference herein.

By the term "polyamine compounds having at least one pendant amine group", what is meant herein is any polyamine compounds having at least one amine group effective to react with the amine reactive material. Specific examples of such polyamine compounds which are suitable for use in the present invention include: polyethylenediamine; a polyethylenimine (such as, for example, polydiethylenetriamine; polytriethylenetetramine, polypentaethylenehexamine or polyhexamethylenediamine); polymethylenedicyclohexylamine; polymethylenedianiline; polytetraethylenepentamine; polyphenylenediamine and blends of two or more of these polyamine compounds. Preferred are those polyamine compounds mentioned above which are water-soluble. While the molecular weight of the polyamine compounds are not believed to be critical, further preferred are those the polyamine compounds mentioned above which have a molecular weight range of from 500 to 100,000 daltons. Most preferred is polyethylenimine.

Those polyamine compounds which are water soluble may be applied to the granular diatomaceous earth from their aqueous solutions, whereas non-water soluble polymers may be applied from organic solvents, such as, for example, methyl alcohol, ethyl alcohol, propyl alcohol.

Generally, for the carrier, at least about 10 mg of polyamine compound is used per gram of the solid support (for example, porous granular diatomaceous earth). Preferably, at least about 15 mg of polyamine compound is used per gram of the solid support.

Generally, for the carrier, no more than about 60 mg of polyamine compound is used per gram of the solid support (for example, porous granular diatomaceous earth). Preferably, no more than about 25 mg of polyamine compound is used per gram of the solid support.

The preferred ratio between the polyamine compound and the diatomaceous earth is about 10 mg to about 60 mg of the polyamine compound per gram of the solid support. Most preferably, this ratio is about 15 mg to about 25 mg of the polyamine compound per gram of the solid support (for example, porous granular diatomaceous earth).

The solution of the polyamine compound used has a concentration of about 1% (weight/volume) to about 0.01% (weight/volume) of polyamine compound to solution solvent (for example, water). The polyamine compound in a solution is added to the granular diatomaceous earth in a ratio of about 10 ml of the granular diatomaceous earth to about 50 ml of the solution of the polyamine compound.

Any solid support suitable for reacting with the polyamine compound and for supporting the treated enzyme of the treated adduct may be utilized herein. It is preferred that such a solid support be porous. In this regard, it is especially preferred that the solid support utilized be porous granular diatomaceous earth.

Any granular diatomaceous earth may be used in accordance with the present invention. A very suitable granular diatomaceous earth has a particle size of greater than about 72 mesh, with a particle size of greater than about 52 being preferred and a particle size of greater than about 40 being the most preferred of all. A very suitable granular diatomaceous earth also has a particle size of smaller than about 10 mesh and, preferably, a particle size of smaller than about 14 mesh. Particularly good results have been obtained with granular diatomaceous earth having a particle size of smaller than about 16 mesh. [Such meshes are as measured on the United States sieve series].

Pore dimensions of granular diatomaceous earth have a radii which are, preferably, in the range of from about 35 angstroms to about 1000 angstroms. The granular diatomaceous earth has a surface area which is, preferably, in the range of from about 20 $m^2/g$ to about 60 $m^2/g$ of granular diatomaceous earth.

The carrier formed as described above is then, preferably, washed using any suitable compound effective to remove free polyamine compound of the carrier. It is preferred that water be used for such washing. Such washing is also well described in the U.S. Pat. No. 4,713,333, the contents of which are hereby incorporated by reference herein.

Separately from the formation of the carrier, the treated adduct is formed. The treated adduct is formed by contacting the enzyme with a solution of an amine reactive material, so that the enzyme is treated with the amine reactive material, forming the treated enzyme-containing adduct.

By the term "amine reactive material" what is meant herein is any compound effective to react with an amine group. The amine reactive material is selected from the group consisting of polyfunctional aldehydes, polyfunctional organic halides, polyfunctional anhydrides, polyfunctional azo compounds, polyfunctional isothiocyanates, polyfunctional isocyanates and blends of two or more of these amine reactive materials.

By the term "polyfunctional" when used to refer to various of the compounds which comprise the amine reactive material, what is meant herein is any compound having or capable of having when contacted with the enzyme, at least two chemical functions effective to react with separate amine groups, one of these functions being capable of reacting with the amine group coming from the polyamine compound of the carrier and the other of these functions being capable of reacting with the amine group coming from the enzyme of the treated adduct.

Generally, the amine reactive material is selected from the group consisting of glutaraldehyde, succindialdehyde, terephthaldehyde, bis-diazobenzidine-2,2'-disulfonic acid, 4,4'-difluoro-3,3'-dinitrodiphenylsulfone, diphenyl-4,4'-dithiocyanate- 2,2'-disulfonic acid, 3-methoxydiphenylmethane-4,4'-diisocyanate, toluene-2-isocyanate-4-isothiocyanate, toluene-2,-4-diisothiocyanate, diazobenzidine, diazobenzidine-3,3'-dianisidine, N,N'-hexamethylene bisiodoacetamide, hexamethylene diisocyanate, cyanuric chloride, 1,5-difluoro-2,4-dinitrobenzene and blends or two or more of these amine reactive materials. Preferably, the amine reactive material is selected from the group consisting of polyfunctional aldehydes. More preferably, the amine reactive material is selected from the group consisting of glutaraldehyde, succindialdehyde, terephthaldehyde. Best results have been obtained with glutaraldehyde.

Those amine reactive materials which are water soluble may be applied to the enzyme from their aqueous solutions. Those amine reactive materials which are not water soluble may be applied to the enzyme from organic solvents, such as, for example, methyl alcohol, ethyl alcohol, propyl alcohol. Water-soluble amine reactive materials are preferred.

Generally, the enzyme is used in an aqueous solution. Preferably, this aqueous solution is a buffered aqueous solution. The selection of precise effective concentrations and precise optimum concentrations of enzyme and the solution composition (for example, aqueous buffer) to be used will vary depending on the enzyme and the solution composition involved. However, such concentrations will be readily apparent to one of ordinary skill in the art, in light of the present disclosure, after simple routine testing. In any event, it is noted here that, preferably, such solutions contain between 70 and 100 ml of the aqueous buffer per ml of enzyme solution (or per gram of a solid enzyme).

Generally, the concentration of the amine reactive material in the solution (water) of the amine reactive material is at least about 0.05% (weight/volume) with at least about 0.1% (weight/volume) being preferred. Further, generally the concentration of the amine reactive material in the solution (water) of amine reactive material is no more than about 0.4% with no more than about 0.2% (weight/volume) being preferred.

The treated adduct has at least about 0.10 g of the amine reactive material per ml of the enzyme solution (before addition of aqueous buffer). Preferably, the treated adduct has at least about 0.15 g of the amine reactive material per ml of the enzyme solution (before addition of the aqueous buffer). Most preferred is the use of at least about 0.2 g of the amine reactive material per ml of the enzyme solution (before addition of the aqueous buffer).

The treated adduct has no more than about 1.50 g of the amine reactive material per ml of the enzyme solution (before addition of the aqueous buffer). Preferably, the treated adduct has no more than about 1.0 g of the amine reactive material per ml of the enzyme solution (before addition of the aqueous buffer). Most preferred is the use of no more than about 0.3 g of the amine reactive material per ml of the enzyme solution (before addition of the aqueous buffer).

However, it is noted here that the ratio between the amine reactive material and the enzyme is dependant upon the enzymatic activity of the enzyme involved.

For example, when glutaraldehyde is the amine reactive material and glucoamylase (containing 200 DU/ml) is the enzyme, at least about 0.15 g of glutaraldehyde per ml of glucoamylase is preferred with at least about 0.2 g of glutaraldehyde per ml of glucoamylase being most preferred, and the use of no more than about 1.00 g of glutaraldehyde per ml of glucoamylase is preferred with the use of no more than 0.3 g of glutaraldehyde per ml of glucoamylase being most preferred.

One Diazyme Unit (DU) is that activity will catalyze the production of one gram of glucose in one hour under the conditions of the assay at pH 4.2 and 60° C. using soluble starch as the substrate.

As another example, when glutaraldehyde is the amine reactive material and fungal α-amylase (containing 40,000 SKBU/g) is the enzyme, at least about 0.15 g of glutaraldehyde per ml of the α-amylase is preferred with at least about 0.2 g of glutaraldehydeper ml of the α-amylase being most preferred, and the use of no more than about 1.00 g of glutaraldehyde per ml of the α-amylase is preferred with the use of no more than 0.3 g of glutaraldehyde per ml of the α-amylase being most preferred.

One α-amylase (SKBU) unit is that activity which will dextrinize 1.0 g of limit-dextrin substrate per hour under the conditions of the assay.

Similarily, and as a final example, when glutaraldehyde is the amine reactive material and β-amylase (containing 1500 units of diastatic activity per ml) is the enzyme, at least about 0.15 g of glutaraldehyde per ml of the β-amylase is preferred with at least about 0.2 g of glutaraldehyde per ml of the β-amylase being most preferred, and the use of no more than about 1.00 g of glutaraldehyde per ml of the β-amylase is preferred with the use of no more than 0.3 g of glutaraldehyde per ml of the β-amylase being most preferred.

The diastatic activity is determined by the method published in Food Chemical Codex, Vol. III (1981) at p. 484, and is expressed as Degrees of Diastatic Power (DP°).

The enzyme is contacted with the amine reactive material (and reacts therewith) at a temperature generally being at least about 10° C. with a temperature of at least about 18° C. being preferred and a temperature of at least about 20° C. being the most preferred. As an upper limit, generally, the temperature is no greater than about 30° C. with no more than about 28° C. being preferred and no more than about 25° C. being most preferred.

The enzyme is contacted with the amine reactive material (and reacts therewith) for a time of at least about 2 hours, with a contact time of at least about 3 hours being preferred and at least about 4 hours being preferred. The enzyme is contacted with the amine reactive material (and reacts therewith for no more than about 24 hours, with a contact time of no more than about 6 hours being preferred and no more than about 4 hours being the most preferred.

The enzyme is contacted with the amine reactive material (and reacts therewith) at a pH which is governed by the pH range the enzyme activity can tolerate without significant loss of enzymatic activity.

When glucoamylase is the enzyme, it is contacted with the amine reactive material (and reacts therewith) at a pH being at least about 3.5, with a pH of at least about 4.5 being preferred, and a pH being no greater than about 6.0, with a pH being no greater than about 5.0 being preferred.

When fungal α-amylase is the enzyme, it is contacted with the amine reactive material (and reacts therewith) at a pH being at least about 4.5, with a pH being at least about 5.0 being preferred, and a pH being no greater than about 7.0, with a pH being no greater than about 5.5 being preferred.

When β-amylase is the enzyme, it is contacted with the amine reactive material (and reacts therewith) at a pH being at least about the range of about 4.5, with a pH of at least about 5.0 being preferred, and a pH being no greater than about 7.0, with a pH being no greater than about 5.5 being preferred.

In a particularly preferred embodiment, the enzyme is contacted with the amine reactive material (and reacts therewith) under agitation for forming the treated enzyme-containing adduct. The enzyme is contacted with the amine reactive material (and reacts therewith) under conditions of mixing to provide a homogeneous mixture through the solution. Preferably, it is sufficient to have a gentle stirring, so that no foaming occurs.

The contacting of the carrier and the treated enzyme containing adduct is performed in such a manner and under such conditions as to permit the carrier and the treated adduct to react with one another, forming the immobilized enzyme conjugate.

Generally, the immobilized enzyme conjugates of the present invention include at least about 0.05 ml of the treated enzyme-containing adduct per gram of the carrier, with at least 0.07 ml of the treated enzyme-containing adduct per gram of the carrier being preferred. Further the immobilized enzyme conjugates of the present invention include no more than about 0.6 ml of the treated enzyme-containing adduct per gram of the carrier, with no more than about 0.5 ml of the treated enzyme-containing adduct per gram of the carrier being preferred.

Where a treated adduct that is formed with a treated glucoamylase and glutaraldehyde is contacted with a carrier formed by polyethylenimine and granular diatomaceous earth, the preferred ratio is of from about 0.11 ml to about 0.13 ml of treated adduct per g of carrier. Where a treated adduct that is formed with treated fungal α-amylase and glutaraldehyde is contacted with a carrier formed by polyethylenimine and granular diatomaceous earth, the preferred ratio is of from about 0.14 ml to about 0.16 ml of treated adduct per g of carrier. Where a treated adduct that is formed with treated β-amylase and glutaraldehyde is contacted with a carrier formed by polyethylenimine and granular diatomaceous earth, the preferred ratio is of from about 0.15 ml to about 0.17 ml of treated adduct per g of carrier.

The carrier and the treated enzyme-containing adduct are contacted with agitation or by recirculation. It is sufficient to have a gentle agitation.

The carrier and the treated enzyme-containing adduct are contacted at a temperature being at least about 5° C., with a temperature of at least about 15° C. being preferred and a temperature of at least 20° C. being especially preferred. The carrier and the treated enzyme-containing adduct are contacted at a temperature being no greater than about 30° C., with a temperature of no greater than about 28° C. being preferred and a temperature of no greater than about 25° C. being especially preferred.

The carrier and the treated enzyme-containing adduct are contacted for at least about 2 hours, with at least about 4 hours being preferred. The carrier and the treated enzyme-containing adduct are contacted for no more than about 24 hours, with no more than about 6 hours being preferred and a period of no more than about 4 hours being especially preferred.

The carrier and the treated enzyme-containing adduct are contacted at a pH of at least about 4.0, with a pH of at least about 4.5 being preferred. The carrier and the treated enzyme-containing adduct are contacted at a pH being no greater than about 7.0, with a pH of no greater than about 6.0 being preferred.

It is further especially preferred that the immobilized enzyme conjugate so obtained be washed with a suitable solution effective to remove free adduct and free carrier. Preferably this solution is water. This step of washing was realized under the same conditions that the step of contacting the carrier and the treated enzyme-containing adduct described above.

The immobilized enzyme conjugate can be stored under refrigeration without an appreciable loss of enzymatic activity over a period of several months. Preferably, before storing the conjugate, a composition in 0.02M acetate at a pH of 4.2 containing 0.3% (weight/volume) sodium benzoate, 0.15% (weight/volume) potassium sorbate and 5% (weight/volume) corn syrup solids is added to the immobilized enzyme conjugate.

One of the unexpected observations of the present invention is that the immobilized enzyme conjugates obtained with the method described above are substantially more stable (as determined by measurement of the percentage of enzymatic activity that the conjugate loses to the reaction medium during the use thereof) than those immobilized enzyme conjugates obtained according to U.S. Pat. No. 4,713,333. Further, they exhibit better thermostability than the immobilized enzyme conjugate prepared according to U.S. Pat. No. 4,713,333. Finally, in the same conditions of use, the half-life of the immobilized enzyme conjugate prepared according to the present invention is greater than the half-life of the immobilized enzyme conjugate prepared according to U.S. Pat. No. 4,713,333. This presents a significant improvement in the productivity of the enzyme.

Another desirable aspect of the present invention is that the immobilized enzyme conjugates disclosed herein can be easily recovered and prepared for reuse by immobilization after regeneration using a simple process involving a base-acid wash. Typically, the used immobilized enzyme conjugate is slurried in water, 0.5N NaOH, water, 0.5N HCl and then water. This aspect of the present invention is significant because it eliminates disposal problems associated therewith, as well as providing a potential economic savings by increasing the productivity of the enzyme.

The present invention is further illustrated by the following examples. The examples are intended to illustrate the preferred embodiments and are not meant to be read as limiting the invention thereby.

EXAMPLE 1

Preparation of an Immobilized Glucoamylase Conjugate. 700 ml of 16 to 40 mesh (United States mesh) porous granular diatomaceous earth (described in U.S. Pat. No. 4,713,333, which is herein incorporated by reference) is transferred to a glass column reactor of 5 cm diameter and 100 cm height.

A 4 cm bed of 12 mesh gravel (aquarium gravel) is placed on the column endplate to help distribute the liquid during upflow of the solutions during the process.

Water is pumped upflow at a rate to expand or fluidize the granular diatomaceous earth about 20% to remove fines. Generally, within a hour the water effluent is free of fines. Water is drained to the top of the granular diatomaceous earth bed.

Then, a 3500 ml of a 0.1% weight/volume aqueous solution of polyethylenimine (PEI-600, molecular weight 40,000–60,000 daltons having a pH of 9.8), is pumped upflow, and recycling the effluent through the bed for 2 hours. The aqueous solution of polyethylenimine is then drained from the column to the top of the bed of the granular diatomaceous earth.

The granular diatomaceous earth is then washed upflow with water for 2 hours to remove free polyethylenimine at room temperature. In this manner, the granular diatomaceous earth-polyethylenimine carrier is obtained.

35 ml of the glucoamylase, sold under the trademark DIAZYME L-200 (SOLVAY ENZYMES, Inc., Elkhart, Ind.) is added to 3500 ml of 0.02M acetate buffer at a pH of 5.0. The glucoamylase DIAZYME L-200 contains 200 DU/ml of glucoamylase activity.

17.5 g of 50% (weight/weight) glutaraldehyde (in water) is then slowly added to the aqueous solution of glucoamylase with gentle mixing, and the glutaraldehyde was allowed to react with the aqueous glucoamylase solution for 4 hours at a temperature of 20°–25° C. and with gentle agitation. The result is the formation of a treated glucoamylase-glutaraldehyde adduct which contains a treated glucoamylase.

The treated glucoamylase-glutaraldehyde adduct was then recirculated through the granular diatomaceous earth-polyethylenimine carrier prepared above. This recirculation was maintained for 4 hours at a temperature of about 20°–25° C. under gentle agitation and excess treated adduct was then washed out of the carrier with water. The result was the formation of a stable, active immobilized glucoamylase conjugate.

The washed conjugate was then removed from the column and stored in 0.02M acetate at a pH of 4.2 containing 0.3% (weight/volume) sodium benzoate, 0.15% (weight/volume) potassium sorbate and 5% (weight/volume) corn syrup solids for future use.

The immobilized glucoamylase conjugate formed as described above may then be stored under refrigeration without an appreciable loss of activity over a period of several months.

The immobilized enzyme conjugate was assayed at a temperature of 55° C. using as substrate 50 ml of 30% (w/v) corn starch in 0.02M acetate at a pH of 4.2. To carry out the assay, the substrate and enzyme were placed in 250 ml flask and incubated in a 55° C. shaker water bath. At 15 and 75 minutes of reaction time, a 0.2 ml aliquot of reaction mixture was removed and added to 0.5 ml of 0.2N $H_2SO_4$ to terminate the reaction. These samples were then diluted by addition of 5.3 ml of distilled water, and then filtered through 0.45µ filter. The products were analyzed by carbohydrate high pressure liquid chromatography (HPLC). One unit of activity represents the amount of enzyme which will produce one micromole of glucose in one minute under the conditions of the assay, and is reported as U/g (units of activity per gram of conjugate).

Enzymatic activity of this preparation was found to be 881 units/g on dry weight basis. It was found that 84.6% of the total activity was expressed as immobilized enzyme and 15.4% was not immobilized. The density of the immobilized enzyme was 0.43 g/ml.

EXAMPLE 2

Stability of the Immobilized Glucoamylase Conjugate in an Extraction Media

This example demontrates the stability of the conjugate (how well the enzyme is tightly-held in the conjugate). The principle of this method is to incubate the immobilized enzyme conjugate in extraction media. After such incubation, the conjugate was removed and the extraction media assayed to determine the quantity of the enzyme therein (as determined by measurement of the enzymatic activity thereof) which was dissociated (unbonded) from the conjugate and lost to the extraction media.

5 ml sample of immobilized enzyme conjugate, prepared according to example 1, was placed into a 15 ml conical plastic tube and washed several times with water. The liquid was then decanted and 5 ml of 0.02N acetate buffer at a pH of 5.0 containing 5% (weight/volume) NaCl was subsequently added.

After mixing several minutes, the tube was incubated 18 hours in 30° C. water bath. After the incubation, the enzyme slurry was gravity filtered through WHATMAN No. 1 filter paper.

Then, 0.1 ml of the filtrate was added to 1.0 ml substrate (20% w/v corn starch in 0.02N acetate at a pH of 5.0), and placed in a 60° C. water bath for 60 minutes. After 60 minutes, the reaction was terminated by placing the tube in a boiling water bath for 10 minutes.

The sample (designated sample A) was then diluted ten fold with mobile phase of 0.01N $H_2SO_4$ and the carbohydrate profile analyzed by HPLC.

For comparison, a sample (designated sample B) of immobilized glucoamylase conjugate was prepared in accordance with Example 1 of U.S. Pat. No. 4,713,333 and was tested in the same manner as described in the paragraph above.

The results of the assays of samples A and B are given in Table 1.

TABLE 1

| Sample | Initial activity U/ml | Post Extraction activity U/ml | Activity Lost % |
| --- | --- | --- | --- |
| A | 379 | 369 | 2.6 |
| B | 332 | 293 | 12.0 |

The results clearly show that the treated glucoamylase of the immobilized glucoamylase conjugate made according to the method of the present invention is clearly more stable (tightly held) in the matrix of the conjugate than those of the immobilized glucoamylase conjugates made according to U.S. Pat. No. 4,713,333, thereby reducing the loss of the enzyme from the conjugate and into the reaction medium, which is experienced by the conjugates of the present invention.

EXAMPLE 3

Stability of the Immobilized Glucoamylase Conjugate in a Glass Column 50 ml of the immobilized glucoamylase conjugate prepared as described above in example 1 was placed in a jacketed glass column of 1.5 cm diameter and 50 cm height.

The column was maintained at a temperature of 55° C. by means of a circulating water bath. An extraction media, composed of 10 % (w/w) dry solids (DS) 43 DE syrup and 5% (w/v) NaCl in 0.02N acetate buffer at a pH of 5.0, was then passed through the column at a temperature of 55° C. at 50 ml/hour flow rate for 24 hours.

At the end of the extraction, the sample (designated sample C) of the immobilized glucoamylase conjugate thus obtained was then assayed to evaluate its stability.

For comparison, a sample (designated sample D) of immobilized glucoamylase conjugate, prepared in accordance with Example 1 of U.S. Pat. No. 4,713,333 was tested in the same manner as described in the paragraph above.

Results of the assay of samples C and D are given in Table 2.

TABLE 2

| Sample | Initial activity U/g | Post extraction activity U/g | Activity lost % |
|---|---|---|---|
| C | 881 | 653 | 26 |
| D | 771 | 396 | 49 |

The results clearly show that the treated glucoamylase of the immobilized glucoamylase conjugate made according to the method of the present invention is clearly more stable (tightly-held) in the matrix of the conjugate than those of the immobilized glucoamylase conjugates made according to U.S. Pat. No. 4,713,333, thereby reducing the loss of the enzyme from the conjugate and into the reaction medium which is experienced by the conjugates of the present invention.

EXAMPLE 4

Preparation of an Immobilized α-Amylase Conjugate 44 ml of the fungal α-amylase sold under the trademark CLARASE L-40,000 by SOLVAY-ENZYMES, Inc. (Elkhart, Ind.), was prepared and formed into a sample (designated sample E) of an immobilized fungal α-amylase conjugate by the immobilization procedure of Example 1.

The fungal α-amylase sold under the trademark CLARASE L-40,000 has an enzyme activity of 40,000 SKBU/g. One (SKBU) α-amylase unit is that activity which will dextrinize 1.0 g of limit-dextrin substrate per hour under the conditions of the assay.

The activity of the immobilized enzyme conjugate was found to be 638 U/g.

EXAMPLE 5

Stability of the Immobilized α-Amylase Conjugate in an Extraction Media 5 ml sample of the immobilized enzyme conjugate, prepared according to Example 4, was prepared and assayed following the assay procedure for assaying enzyme activity described above in Example 1, except that the pH of the substrate was 6.0.

The stability of the immobilized fungal α-amylase conjugate was evaluated as described in Example 2 by incubating the enzyme overnight at a temperature of 30° C. The pH of the NaCl acetate buffer was 6.0 as opposed to a pH of 5.0 for the immobilized glucoamylase of Example 1, and the temperature for assaying the solubilized fungal α-amylase activity was 50° C. instead of 60° C.

For comparison, a sample (designated sample F) of immobilized fungal α-amylase conjugate, prepared in accordance with the method used in Example 1 of U.S. Pat. No. 4,713,333, was tested in the same manner as described in the paragraph above.

Results of the assays of the samples E and F are given in Table 3.

TABLE 3

| Sample | Initial activity U/ml | Post Extraction activity U/ml | Activity Lost % |
|---|---|---|---|
| E | 274 | 266.5 | 3.0 |
| F | 366 | 156.0 | 57.0 |

The results clearly show that the treated α-amylase of the immobilized α-amylase conjugate made according to the method of the present invention is clearly more stable (tightly-held) in the matrix of the conjugate than those of the immobilized fungal α-amylase conjugates prepared according to U.S. Pat. No. 4,713,333, thereby reducing the loss of the enzyme from the conjugate and into the reaction medium which is experienced by the conjugate of the present invention.

EXAMPLE 6

Stability of the Immobilized α-Amylase Conjugate in a Glass Column 50 ml of the immobilized α-Amylase conjugate prepared as described above in example 4 was obtained (designated sample E).

For comparison, a sample (designated sample F) of immobilized α-Amylase conjugate, prepared in accordance with Example 1 of U.S. Pat. No. 4,713,333 was also prepared.

The stabilities of the both samples (samples E and F) of the immobilized fungal α-amylase conjugates were examined by the column method described in Example 3 except that the pH of the 10% DS (dry solids) syrup in 0.02M acetate at 5.0% (w/v) NaCl was 6.0 instead of 5.0, and the column temperature was 50° C. instead of 55° C.

Results of the assays of the samples E and F using the column method are given in Table 4.

TABLE 4

| Sample | Initial activity U/g | Post extraction activity U/g | Activity lost % |
| --- | --- | --- | --- |
| E | 638 | 608 | 4.7 |
| F | 851 | 518 | 39.0 |

The results clearly show that the treated fungal α-amylase of the immobilized fungal α-amylase conjugate made according to the present invention is clearly more stable (tightly-held) in the matrix of the conjugate than those of the immobilized fungal α-amylase conjugates made according to U.S. Pat. No. 4,713,333, thereby reducing the loss of the enzyme from the conjugate and into the reaction medium which is experienced by the conjugates of the present invention.

EXAMPLE 7

Stability (Half-Life) of the Immobilized α-Amylase Conjugate

Another method to observe stability is to place the immobilized enzyme conjugate in a column and then monitor the activity as substrate is passed through the enzyme conjugate bed.

A 15 ml quantity of the immobilized fungal α-amylase conjugate (designated sample G) obtained as described above in Example 4 was placed in a glass jacket column of 1.5 cm diameter and 50 cm height. The column was maintained at a temperature of 60° C. and the feed syrup was percolated through the bed at a constant flow rate of about 45 ml per hour. The feed syrup was composed of 40% DS (dry solids) of 43 DE syrup adjusted to a pH of 6.0 and the following preservatives were added: 0.3% (w/v) sodium benzoate, 0.15% (w/v) potassium sorbate, 125 ppm methyl paraben and 250 ppm $SO_2$.

Daily samples were taken and the carbohydrate profile was obtained by HPLC analysis. The disaccharide fraction was used to calculate the activity by calculating the μmoles as maltose formed per minute per ml of immobilized enzyme conjugate.

For comparison, a sample (designated sample H) of immobilized fungal α-amylase conjugate, prepared in accordance with the method used in Example 1 of U.S. Pat. No. 4,713,333, was tested in the same manner as described in the paragraph above.

Results of the assay of samples G and H are given in Table 5.

TABLE 5

| Sample | Initial activity U/ml | Half-life days |
| --- | --- | --- |
| G | 1700 | 29 |
| H | 1500 | 18 |

The results clearly show that the treated fungal α-amylase of the immobilized fungal α-amylase conjugate prepared according to the present invention is clearly more stable than the immobilized fungal α-amylase conjugate prepared according to U.S. Pat. No. 4,713,333 in that it exhibits a greatly increased half-life.

EXAMPLE 8

Preparation of an Immobilized β-Amylase Conjugate 48 ml of the β-amylase, containing 1500 units of diastatic activity per ml, was prepared and formed into a sample (designated sample I) of an immobilized β-amylase conjugate by the immobilization procedure of Example 1.

The activity was determined by the method for diastatic activity published in Food Chemical Codex, Vol. III, (1981), p. 484, and is expressed as Degrees of Diastatic Power Enzymatic activity of this preparation is found to be 860 units/g on dry weight basis.

EXAMPLE 9

Stability of the Immobilized β-Amylase Conjugate in an Extraction Media 5 ml sample (designated sample I) of the immobilized enzyme conjugate, prepared according to Example 8, was prepared and assayed following the assay procedure for assaying enzyme activity described above in Example 1, except that the pH of the substrate was 5.5.

The stability of the immobilized β-amylase conjugate was evaluated as described in Example 2 by incubating the enzyme overnight at a temperature of 30° C. The pH of the NaCl acetate buffer was 5.5 as opposed to a pH of 5.0 for the immobilized glucoamylase of Example 2, and the temperature for assaying the solubilized β-amylase activity was 55° C. instead of 60° C.

For comparison, a sample (designated sample J) of immobilized β-amylase conjugate, prepared in accordance with the method used in Example 1 of U.S. Pat. No. 4,713,333, was tested in the same manner as described in the paragraph above.

Results of the assay of the samples I and J are given in Table 6.

TABLE 6

| Sample | Initial activity U/ml | Post Extraction activity U/ml | Activity Lost % |
| --- | --- | --- | --- |
| I | 370 | 369 | <0.5 |
| J | 201 | 188 | 6.5 |

The results clearly show that the treated β-amylase of the immobilized β-amylase conjugate made according to the invention is clearly more stable (tightly-held) in the matrix of the conjugate than those of the immobilized β-amylase conjugates made according to U.S. Pat. No. 4,713,333, thereby reducing the loss of the enzyme from the conjugate and into the reaction medium which is experienced by the conjugates of the present invention.

Obviously, numerous modifications and variations of the present invention are possible in light of the above teachings. It is therefore to be understood that, within the scope of the appended claims, the invention may be practiced otherwise than as specifically described herein.

What is claimed is:

1. A treated liquid adduct for preparing an immobilized enzyme conjugate, wherein the treated liquid adduct includes at least one amine reactive material selected from the group consisting of polyfunctional aldehydes, polyfunctional organic halides, polyfunctional anhydrides, polyfunctional azo compounds, polyfunctional isothiocyanates, polyfunctional isocyanates and blends of two or more of these amine reactive materials and wherein the treated liquid adduct further includes at least one enzyme contacted with the at least one amine reactive material, whereby the at least one enzyme is treated and a treated enzyme-containing liquid adduct is formed.

2. A method for preparing an immobilized enzyme conjugate comprising the steps of:

(a) contacting porous, granular diatomaceous earth with a solution of a polyamine compound having at least one pendant amine group to form a carrier;

(b) contacting an enzyme with a solution of at least one amine reactive material selected from the group consisting of polyfunctional aldehydes, polyfunctional organic halides, polyfunctional anhydrides, polyfunctional azo compounds, polyfunctional isothiocyanates, polyfunctional isocyanates and blends of two or more of these amine reactive materials, to form a treated enzyme-containing liquid adduct;

(c) contacting the carrier and the treated enzyme-containing liquid adduct, so that the carrier and the treated enzyme-containing liquid adduct react to form an immobilized enzyme conjugate.

3. The method of claim 2, wherein said enzyme is a member selected from the group consisting of glucoamylase, fungal α-amylase and β-amylase.

4. The method of claim 2, wherein step (b) is carried out under conditions which include agitation.

5. The method of claim 2, wherein the immobilized enzyme conjugate is washed with water after step (c).

6. An immobilized enzyme conjugate produced by the method of claim 1.

7. The immobilized enzyme conjugate of claim 6, wherein said enzyme is a member selected from the group consisting of glucoamylase, fungal α-amylase and β-amylase.

8. An immobilized enzyme conjugate comprising a carrier and a treated enzyme-containing liquid adduct, the carrier including a polyamine compound having at least one pendant amine group and a solid support bonded to the polyamine compound, whereby a carrier is formed, the treated enzyme-containing liquid adduct including at least one amine reactive material selected from the group consisting of polyfunctional aldehydes, polyfunctional organic halides, polyfunctional anhydrides, polyfunctional azo compounds, polyfunctional isothiocyanates, polyfunctional isocyanates and blends of two or more of these amine reactive materials and the treated enzyme-containing liquid adduct further including at least one enzyme contacted with the at least one amine reactive material, whereby the at least one enzyme is treated and a treated enzyme-containing liquid adduct is formed, and the carrier being bonded to the treated enzyme-containing liquid adduct, whereby a stable, active immobilized enzyme conjugate is formed.

9. The immobilized enzyme conjugate of claim 8, wherein said at least one enzyme is a member selected from the group consisting of: glucoamylase, fungal α-amylase and β-amylase.

10. The immobilized enzyme conjugate of claim 8, wherein the at least one amine reactive material is glutaraldehyde.

11. The immobilized enzyme conjugate of claim 8, wherein the polyamine compound is polyethylenimine.

12. The immobilized enzyme conjugate of claim 8, wherein the at least one enzyme contains an amino group capable of reacting with the at least one amine reactive material.

13. The immobilized enzyme conjugate of claim 8, wherein the ratio between the at least one amine reactive material and the at least one enzyme is from about 0.10 g to about 1.50 g of the at least one amine reactive material per ml of the enzyme.

14. The immobilized enzyme conjugate of claim 8, wherein the ratio between the treated enzyme-containing liquid adduct and the carrier is from about 0.05 ml to about 0.6 ml of treated enzyme-containing liquid adduct per g of carrier.

15. An immobilized enzyme conjugate comprising a carrier and a treated enzyme-containing liquid adduct, the treated enzyme-containing liquid adduct including at least one amine reactive material selected from the group consisting of polyfunctional aldehydes, polyfunctional organic halides, polyfunctional anhydrides, polyfunctional azo compounds, polyfunctional isothiocyanates, polyfunctional isocyanates and blends of two or more of these amine reactive materials, and the treated enzyme-containing liquid adduct further including at least one enzyme contacted with the at least one amine reactive material, whereby the at least one enzyme is treated and a treated enzyme-containing liquid adduct is formed, and the carrier being a solid support which is bonded to the treated enzyme-containing liquid adduct, whereby a stable, active immobilized enzyme conjugate is formed.

16. The immobilized enzyme conjugate of claim 15, wherein said at least one enzyme is a member selected from the group consisting of: glucoamylase, fungal α-amylase and β-amylase.

17. The immobilized enzyme conjugate of claim 15, wherein the at least one amine reactive material is glutaraldehyde.

18. The immobilized enzyme conjugate of claim 15, wherein the polyamine compound is polyethylenimine.

19. The immobilized enzyme conjugate of claim 15, wherein the at least one enzyme contains an amino group capable of reacting with the at least one amine reactive material.

20. The immobilized enzyme conjugate of claim 15, wherein the ratio between the at least one amine reactive material and the at least one enzyme is from about 0.10 g to about 1.50 g of the at least one amine reactive material per ml of the enzyme.

21. The immobilized enzyme conjugate of claim 15, wherein the ratio between the treated enzyme-containing liquid adduct and the carrier is from about 0.05 ml to about 0.6 ml of treated enzyme-containing liquid adduct per g of carrier.

22. The immobilized enzyme conjugate of claim 15, wherein the solid support carrier is water-insoluble.

* * * * *